(12) United States Patent
Hoeppner

(10) Patent No.: US 8,518,272 B2
(45) Date of Patent: Aug. 27, 2013

(54) STERILE BLOOD SEPARATING SYSTEM

(75) Inventor: Jacy C. Hoeppner, Warsaw, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 954 days.

(21) Appl. No.: 12/062,801

(22) Filed: Apr. 4, 2008

(65) Prior Publication Data

US 2009/0250413 A1  Oct. 8, 2009

(51) Int. Cl.
*B01D 21/26* (2006.01)
*C02F 1/38* (2006.01)

(52) U.S. Cl.
USPC ........ 210/787; 210/121; 210/512.1; 210/513; 494/44; 494/50; 604/19

(58) Field of Classification Search
USPC .............. 210/513, 121, 787, 782, 109, 512.1, 210/512.3, 518; 494/37, 35, 43, 83
See application file for complete search history.

(56) References Cited

U.S. PATENT DOCUMENTS

| | | |
|---|---|---|
| 1,378,806 A | 5/1921 | Ausubel |
| 1,948,388 A | 2/1934 | Liberson |
| 1,950,137 A | 3/1934 | Dowe |
| 2,112,160 A | 3/1938 | Johnson |
| 2,322,753 A | 6/1943 | Thomas |
| 2,533,004 A | 12/1950 | Ferry et al. |
| 2,915,063 A | 12/1959 | Cutter |
| RE25,113 E | 1/1962 | Wilburn |
| 3,112,747 A | 12/1963 | Cowley |
| 3,215,141 A | 11/1965 | Podhora |
| 3,223,083 A | 12/1965 | Cobey |
| 3,236,418 A | 2/1966 | Dalle et al. |
| 3,314,427 A | 4/1967 | Stafford |
| 3,406,686 A | 10/1968 | Keller |
| 3,435,944 A | 4/1969 | Ishii |
| 3,467,096 A | 9/1969 | Horn |
| 3,473,646 A | 10/1969 | Burke |
| 3,552,394 A | 1/1971 | Horn |
| 3,586,064 A | 6/1971 | Brown et al. |
| 3,625,353 A | 12/1971 | Ishii |
| 3,654,925 A | 4/1972 | Holderith |
| 3,685,248 A | 8/1972 | Godelaine |

(Continued)

FOREIGN PATENT DOCUMENTS

| | | |
|---|---|---|
| CA | 2244697 | 8/1997 |
| CA | 2295733 A1 | 1/1999 |

(Continued)

OTHER PUBLICATIONS

"The New Gold Standard" brochure for GPS® Mini and GPS®II Platelet Concentrate Separation Kit with ACD-A Anticoagulant, Biomet Biologics, Inc. (Dec. 2006), 7 pages.

(Continued)

*Primary Examiner* — Dirk Bass
(74) *Attorney, Agent, or Firm* — Harness, Dickey

(57) ABSTRACT

A system for separating components of a composition according to density. The system includes a torque generating device, a separation device, and a housing. The separation device separates the composition into different components according to density. The housing accommodates the separation device. The housing includes a base having an interface that transfers torque from the torque generating device to the separation device, a cover, and a conduit for introducing the composition into the separation device without opening the cover.

20 Claims, 3 Drawing Sheets

(56) References Cited

U.S. PATENT DOCUMENTS

| | | |
|---|---|---|
| 3,767,085 A | 10/1973 | Cannon et al. |
| 3,780,935 A | 12/1973 | Lukacs et al. |
| 3,800,947 A | 4/1974 | Smith |
| 3,828,980 A | 8/1974 | Creighton et al. |
| 3,894,952 A | 7/1975 | Ayres |
| 3,937,219 A | 2/1976 | Karakashian |
| 3,976,073 A | 8/1976 | Quick et al. |
| 4,021,352 A | 5/1977 | Sarstedt et al. |
| 4,040,420 A | 8/1977 | Speer |
| 4,057,499 A | 11/1977 | Buono |
| 4,121,739 A | 10/1978 | Devaney et al. |
| 4,142,668 A | 3/1979 | Lee |
| 4,184,593 A | 1/1980 | Dorr et al. |
| 4,202,769 A | 5/1980 | Greenspan |
| 4,226,235 A | 10/1980 | Sarnoff et al. |
| 4,260,077 A | 4/1981 | Schroeder |
| 4,269,174 A | 5/1981 | Adair |
| 4,322,298 A | 3/1982 | Persidsky |
| 4,359,049 A | 11/1982 | Redl et al. |
| 4,375,272 A | 3/1983 | Sutton, III |
| 4,413,773 A | 11/1983 | Rohde et al. |
| 4,424,132 A | 1/1984 | Iriguchi et al. |
| 4,434,820 A | 3/1984 | Glass |
| 4,465,476 A | 8/1984 | Gahwiler et al. |
| 4,467,588 A | 8/1984 | Carveth |
| 4,498,904 A | 2/1985 | Turner et al. |
| 4,524,770 A | 6/1985 | Orandi |
| 4,610,666 A | 9/1986 | Pizzino |
| 4,627,879 A | 12/1986 | Rose et al. |
| 4,628,969 A | 12/1986 | Jurgens, Jr. et al. |
| 4,631,055 A | 12/1986 | Redl et al. |
| 4,650,468 A | 3/1987 | Jennings, Jr. |
| 4,673,395 A | 6/1987 | Phillips et al. |
| 4,714,457 A | 12/1987 | Alterbaum |
| 4,734,261 A | 3/1988 | Koizumi et al. |
| 4,735,616 A | 4/1988 | Eibl et al. |
| 4,744,955 A | 5/1988 | Shapiro |
| 4,767,026 A | 8/1988 | Keller et al. |
| 4,818,386 A | 4/1989 | Burns |
| 4,822,340 A | 4/1989 | Kamstra et al. |
| 4,826,048 A | 5/1989 | Skorka et al. |
| 4,828,716 A | 5/1989 | McEwen et al. |
| 4,874,368 A | 10/1989 | Miller et al. |
| 4,877,520 A | 10/1989 | Burns |
| 4,878,903 A | 11/1989 | Mueller |
| 4,902,281 A | 2/1990 | Avoy |
| 4,907,019 A | 3/1990 | Stephens |
| 4,932,942 A | 6/1990 | Maslanka et al. |
| 4,957,637 A | 9/1990 | Cornell |
| 4,978,336 A | 12/1990 | Capozzi et al. |
| 4,979,942 A | 12/1990 | Wolf et al. |
| 5,032,117 A | 7/1991 | Motta |
| 5,033,252 A | 7/1991 | Carter |
| 5,049,135 A | 9/1991 | Davis |
| 5,074,844 A | 12/1991 | Zdeb et al. |
| 5,080,262 A | 1/1992 | Herold et al. |
| 5,104,375 A | 4/1992 | Wolf et al. |
| 5,104,387 A | 4/1992 | Pokorney et al. |
| 5,116,315 A | 5/1992 | Capozzi et al. |
| 5,147,323 A | 9/1992 | Haber et al. |
| 5,152,905 A | 10/1992 | Pall et al. |
| 5,160,021 A | 11/1992 | Sibley et al. |
| 5,176,658 A | 1/1993 | Ranford |
| 5,217,118 A | 6/1993 | Mochizuki et al. |
| 5,226,558 A | 7/1993 | Whitney et al. |
| 5,226,877 A | 7/1993 | Epstein |
| 5,226,887 A | 7/1993 | Farr et al. |
| 5,253,785 A | 10/1993 | Haber et al. |
| 5,286,257 A | 2/1994 | Fischer |
| 5,290,259 A | 3/1994 | Fischer |
| 5,292,318 A | 3/1994 | Haber et al. |
| 5,298,024 A | 3/1994 | Richmond |
| 5,300,041 A | 4/1994 | Haber et al. |
| 5,308,041 A | 5/1994 | Griffioen et al. |
| 5,314,412 A | 5/1994 | Rex et al. |
| 5,318,524 A | 6/1994 | Morse et al. |
| 5,322,510 A | 6/1994 | Lindner et al. |
| 5,332,092 A | 7/1994 | Fischer |
| 5,354,483 A | 10/1994 | Furse |
| 5,361,906 A | 11/1994 | Sterett |
| 5,368,563 A | 11/1994 | Lonneman et al. |
| 5,372,586 A | 12/1994 | Haber et al. |
| 5,376,079 A | 12/1994 | Holm et al. |
| 5,390,792 A | 2/1995 | Van Ness et al. |
| 5,393,497 A | 2/1995 | Haber et al. |
| 5,393,674 A | 2/1995 | Levine et al. |
| 5,409,465 A | 4/1995 | Boggs et al. |
| 5,411,465 A | 5/1995 | Glen et al. |
| 5,419,491 A | 5/1995 | Breitsprecher |
| 5,420,250 A | 5/1995 | Lontz |
| 5,445,614 A | 8/1995 | Haber et al. |
| 5,454,793 A | 10/1995 | Levander et al. |
| 5,464,396 A | 11/1995 | Barta et al. |
| 5,474,540 A | 12/1995 | Miller et al. |
| 5,478,323 A | 12/1995 | Westwood et al. |
| 5,480,068 A | 1/1996 | Frazier et al. |
| 5,484,431 A | 1/1996 | Scharf et al. |
| 5,505,704 A | 4/1996 | Pawelka et al. |
| 5,510,102 A | 4/1996 | Cochrum |
| 5,519,422 A | 5/1996 | Thoman et al. |
| 5,519,931 A | 5/1996 | Reich |
| 5,520,657 A | 5/1996 | Sellers et al. |
| 5,520,658 A | 5/1996 | Holm et al. |
| 5,522,804 A | 6/1996 | Lynn |
| 5,530,531 A | 6/1996 | Girard |
| 5,542,934 A | 8/1996 | Silver |
| 5,549,651 A | 8/1996 | Lynn |
| 5,582,596 A | 12/1996 | Fukunaga et al. |
| 5,585,007 A | 12/1996 | Antanavich et al. |
| 5,597,530 A | 1/1997 | Smith et al. |
| 5,605,255 A | 2/1997 | Reidel et al. |
| 5,605,541 A | 2/1997 | Holm |
| 5,638,661 A | 6/1997 | Banks |
| 5,643,206 A | 7/1997 | Fischer |
| 5,656,035 A | 8/1997 | Avoy |
| 5,665,067 A | 9/1997 | Linder et al. |
| 5,697,915 A | 12/1997 | Lynn |
| 5,728,075 A | 3/1998 | Levander et al. |
| 5,752,626 A | 5/1998 | Bachand |
| 5,759,169 A | 6/1998 | Marx |
| 5,759,171 A | 6/1998 | Coelho et al. |
| 5,792,103 A | 8/1998 | Schwartz et al. |
| 5,810,885 A | 9/1998 | Zinger et al. |
| 5,814,022 A | 9/1998 | Antanavich et al. |
| 5,814,066 A | 9/1998 | Spotnitz |
| 5,819,988 A | 10/1998 | Sawhney et al. |
| 5,824,012 A | 10/1998 | Burchett et al. |
| 5,830,547 A | 11/1998 | MacKenzie et al. |
| 5,842,326 A | 12/1998 | Wolf |
| 5,871,700 A | 2/1999 | Konrad |
| 5,881,536 A | 3/1999 | Muller-Wille et al. |
| 5,888,408 A | 3/1999 | Nagels |
| 5,935,437 A | 8/1999 | Whitmore |
| 5,951,517 A | 9/1999 | Lampropoulos et al. |
| 5,968,018 A | 10/1999 | Freeman et al. |
| 5,976,102 A | 11/1999 | Epstein |
| 5,980,866 A | 11/1999 | Uchida et al. |
| 5,997,811 A | 12/1999 | Esposito |
| 5,997,881 A | 12/1999 | Powell et al. |
| 6,001,259 A | 12/1999 | Whitmore |
| 6,059,749 A | 5/2000 | Marx |
| 6,063,055 A | 5/2000 | Epstein et al. |
| 6,079,868 A | 6/2000 | Rydell |
| 6,099,511 A | 8/2000 | Devos et al. |
| 6,113,571 A | 9/2000 | Zinger et al. |
| 6,123,687 A | 9/2000 | Simonyi et al. |
| 6,132,396 A | 10/2000 | Antanavich et al. |
| 6,206,905 B1 | 3/2001 | Holm et al. |
| 6,234,994 B1 | 5/2001 | Zinger et al. |
| 6,251,370 B1 | 6/2001 | Uchida et al. |
| 6,308,747 B1 | 10/2001 | Farris |
| 6,328,229 B1 | 12/2001 | Duronio et al. |
| 6,331,172 B1 | 12/2001 | Epstein et al. |
| 6,394,982 B1 | 5/2002 | Ehrenfels |

| | | |
|---|---|---|
| 6,471,670 B1 | 10/2002 | Enrenfels et al. |
| 6,475,193 B1 | 11/2002 | Park et al. |
| 6,488,650 B1 | 12/2002 | Epstein et al. |
| 6,544,162 B1* | 4/2003 | Van Wie et al. .................. 494/37 |
| 6,648,133 B1 | 11/2003 | Blaschke et al. |
| 6,711,879 B2 | 3/2004 | Korteweg et al. |
| 6,830,762 B2 | 12/2004 | Baugh et al. |
| 6,959,812 B2 | 11/2005 | Reif et al. |
| 7,179,391 B2 | 2/2007 | Leach et al. |
| 7,223,346 B2 | 5/2007 | Dorian et al. |
| 7,374,678 B2 | 5/2008 | Leach et al. |
| 7,470,371 B2 | 12/2008 | Dorian et al. |
| 7,766,900 B2 | 8/2010 | Leach et al. |
| 2001/0016709 A1 | 8/2001 | Tovey et al. |
| 2002/0035820 A1 | 3/2002 | Farris |
| 2002/0104808 A1 | 8/2002 | Blasetti et al. |
| 2003/0023203 A1 | 1/2003 | Lavi et al. |
| 2003/0029763 A1 | 2/2003 | Reif et al. |
| 2003/0139774 A1 | 7/2003 | Epstein et al. |
| 2004/0024353 A1 | 2/2004 | Petersen et al. |
| 2004/0035743 A1 | 2/2004 | Tighe et al. |
| 2004/0065626 A1 | 4/2004 | Woo |
| 2004/0209755 A1 | 10/2004 | Moore et al. |
| 2005/0247715 A1 | 11/2005 | Ellsworth et al. |
| 2006/0064070 A1 | 3/2006 | Martin |
| 2006/0175242 A1 | 8/2006 | Dorian et al. |
| 2006/0196885 A1 | 9/2006 | Leach et al. |
| 2006/0217674 A1 | 9/2006 | Romano et al. |
| 2006/0273049 A1 | 12/2006 | Leach et al. |
| 2006/0273050 A1* | 12/2006 | Higgins et al. ................. 210/787 |
| 2006/0278588 A1 | 12/2006 | Woodell-May |
| 2007/0012623 A1* | 1/2007 | Robinson et al. ............. 210/647 |
| 2008/0217264 A1 | 9/2008 | Leach et al. |
| 2008/0217265 A1 | 9/2008 | Leach et al. |
| 2008/0283474 A1 | 11/2008 | Leach et al. |
| 2009/0014391 A1 | 1/2009 | Leach et al. |
| 2009/0221075 A1 | 9/2009 | Dorian et al. |
| 2009/0253566 A1 | 10/2009 | Chavarria |
| 2010/0274206 A1 | 10/2010 | Leach et al. |

FOREIGN PATENT DOCUMENTS

| | | |
|---|---|---|
| DE | 632579 | 9/1936 |
| DE | 807113 | 6/1951 |
| DE | 3246999 A1 | 5/1984 |
| DE | 8913761 | 3/1990 |
| DE | 29516650 | 1/1996 |
| EP | 0208053 A2 | 1/1987 |
| EP | 0253418 A1 | 1/1988 |
| EP | 0253949 A2 | 1/1988 |
| EP | 0292472 | 11/1988 |
| EP | 0316284 A1 | 5/1989 |
| EP | 0432871 A2 | 6/1991 |
| EP | 0528949 A1 | 3/1993 |
| EP | 592242 | 4/1994 |
| EP | 0858776 | 8/1998 |
| FR | 840257 A | 4/1939 |
| FR | 2612782 | 9/1988 |
| FR | 2661097 | 10/1991 |
| FR | 2666986 A1 | 3/1992 |
| FR | 2668060 | 4/1992 |
| JP | 08238314 A | 9/1996 |
| JP | 08280802 A | 10/1996 |
| JP | 09108302 A | 4/1997 |
| WO | WO-8807874 | 10/1988 |
| WO | WO-9001959 | 3/1990 |
| WO | WO-9101711 | 2/1991 |
| WO | WO-9117778 A1 | 11/1991 |
| WO | WO-9419038 | 9/1994 |
| WO | WO-9639212 | 12/1996 |
| WO | WO-9725015 A1 | 7/1997 |
| WO | WO-9728834 | 8/1997 |
| WO | WO-9746203 A1 | 12/1997 |
| WO | WO-9747343 A1 | 12/1997 |
| WO | WO-9802098 A1 | 1/1998 |
| WO | WO-9810703 | 3/1998 |
| WO | WO-9810704 | 3/1998 |
| WO | WO-9813094 | 4/1998 |
| WO | WO-9840115 | 9/1998 |
| WO | WO-9901069 | 1/1999 |
| WO | WO-03018425 A1 | 3/2003 |

OTHER PUBLICATIONS

International Search Report mailed Jul. 10, 2009 for PCT/US2009/039488 claiming benefit of U.S. Appl. No. 12/062,817, filed Apr. 4, 2008.

International Preliminary Examination Report issued Oct. 5, 2010 for PCT/US2009/039488 claiming benefit of U.S. Appl. No. 12/062,817, filed Apr. 4, 2008.

Alving, B.M., M.J. Weinstein, et al. (1995). "Fibrin sealant: summary of a conference on characteristics and clinical uses." Transfusion 35(9): 783-90.

B. Braun/McGaw Product Catalog, May 1, 1999.

CFT Cell Factor Technologies, Inc., GPS® II Platelet Concentrate System, 2004 Biomet Orthopedics, Inc. (10 pages).

DePuy AcroMed, Inc., Symphony™ Platelet Concentrate System, 2001.

Developing Technologies for Accelerating Healing, Naturally®, Smart PReP®2, Harvest® Technologies Corp. 2002 (6 pages).

Drug Intelligence and Clinical Pharmacy, vol. 22, pp. 946-952, Dec. 1988, Dennis F. Thompson, et al., "Fibrin Glue: A Review of Its Preparation, Efficacy, and Adverse Effects as a Topical Hemostat".

DynaStat™, Introducing DynaStat™Surgical Hemostat—An Innovation in Hemostatic Biodevices, 2000 Cohesion Technologies, Inc.

FibriJet® 11:1 Ratio Applicator, Micromedics, Inc., printed from www.micromedics-usa.com/products/PDFs/FibriJet_Easy-Assembly.pdf, in 2005 (1 page).

FibriJet® product sheet, Micromedics, Inc., printed from www.micromedics-usa.com/products/PDFs/product_sheet.pdf, in 2005 (2 pages).

FibriJet®Ratio Applicator for application of platelet gel, Micromedics, Inc., printed from www.micromedics-usa.com/products/PDFs/ratio.pdf, in 2005 (1 page).

Matras, H. (1985). "Fibrin seal: the state of the art." J Oral Maxillofac Surg 43(8): 605-11.

Matras, Helene, H. P. Dinges, H. Lassmann, and B. Mamoli. "Zur nahtlosen interfaszikularen Nerventransplantation im Tierexperiment." Wein Med Woschtr 122 (37 1972): 517-523.

OEM Products Catalog, Merit®Medical, available by Jan. 2003.

Prof. H. Stütz, M.D., et al., The Use of Autologous Fibrin Glue to Reduce Perioperative Blood Loss in Total Knee Arthroplasty—Results of a Controlled Study, Translated from the original article published in Orthopädische Praxis 40, 12 (2004).

Redl, H. and G. Schlag (1986). Fibrin Sealant and Its Modes of Application. Fibrin Sealant in Operative Medicine. G. Schlad and H. Redl. Heidelberg, Springer-Verlag: 13-26.

Redl, H.G. Schlag, et al. (1982). "Methods of Fibrin Seal Application." Thorac, cardiovasc. Surgeon 30: 223-227.

Shimada, J.K. Mikami, et al. (1995). "Closure of leaks by fibrin gluing. Effects of various application techniques and temperatures." J Cardiovac Surg (Torino) 35(2): 181-4.

Sierra, D. H. "Fibrin sealant adhesive systems: a review of their chemistry, material properties and clinical applications." *J Biomater Appl* 7 (4 1993): 309-52.

Sporn, L.A., et al., (1995). "Cell proliferation on fibrin: modulation by fibrinopeptide cleavage." Blood 86(5): 1802-10.

Tange, R.A. (1986). "A New Application Method for Fibrin Sealant: The Glue Gun." Fibrin Sealant in Operative Medicine. G. Schlad and H. Redl. Heidelberg, Springer-Verlag.

Vox Sanq, vol. 68: 82-89, Feb. 1995, Boomgaard et. al, Pooled Platelet Concentrates Prepared by the Platelet-Rich-Plasma Method and Filtered with Three Different Filters and Stored for 8 Days.

\* cited by examiner

STERILE BLOOD SEPARATING SYSTEM

FIELD

The present disclosure relates to sterile devices, systems, and methods for separating components of a composition, such as blood.

BACKGROUND

The statements in this section merely provide background information related to the present disclosure and may not constitute prior art.

Whole blood includes a variety of different fractions or parts. For example, human whole blood includes platelet rich plasma (PRP), platelet poor plasma (PPP), red blood cells (RBCs), and white blood cells (WBCs). These different blood fractions have a variety of clinical and experimental uses. There is a need for devices and methods that separate and isolate the different fractions of whole blood. In particular, there is a need for devices and methods for separating and isolating different blood fractions in a non-sterile environment by non-sterile personnel for later use in a sterile environment.

SUMMARY

The present teachings provide for a system for separating components of a composition according to density. The system includes a torque generating device, a separation device, and a housing. The separation device separates the composition into different components according to density. The housing accommodates the separation device. The housing includes a base having an interface that transfers torque from the torque generating device to the separation device, a cover, and a conduit for introducing the composition into the separation device without opening the cover.

The present teachings further provide for a method for separating components of a composition according to density. The method includes: sealing a sterilized separation device within a container having a base and a cover such that the separation device is in cooperation with an interface at the base of the container; inserting the composition into the sterilized separation device sealed within the container by injecting the composition through a conduit that extends through the container and mates with the separation device; mating the container with a torque generating device, the interface in contact with both the torque generating device and the separation device; spinning the separation device using the torque generating device to separate the composition into different components according to density, the separation device is spun independent of the container and torque is transferred from the torque generating device to the separation device by the interface; removing the sterile separation device from the container; and withdrawing at least one of the different components from the separation device as necessary while the separation device is in the sterile environment.

The present teachings also provide for a container for housing a sterile separation device for separating components of a composition according to density. The container includes a container base, an interface, a cover, and a conduit. The container base has sidewalls extending from the container base to define a receptacle for accommodating the separation device. The interface is at the container base for transferring torque from a torque generating device to the separation device when the separation device is seated within the receptacle. The cover covers the receptacle and seals the sterile separation device within the receptacle to prevent contamination of the sterile separation device. The conduit extends through the container to the sterile separation device to permit delivery of blood through the container and into the sterile separation device when the sterile separation device is sealed within the receptacle.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

Figure 1:
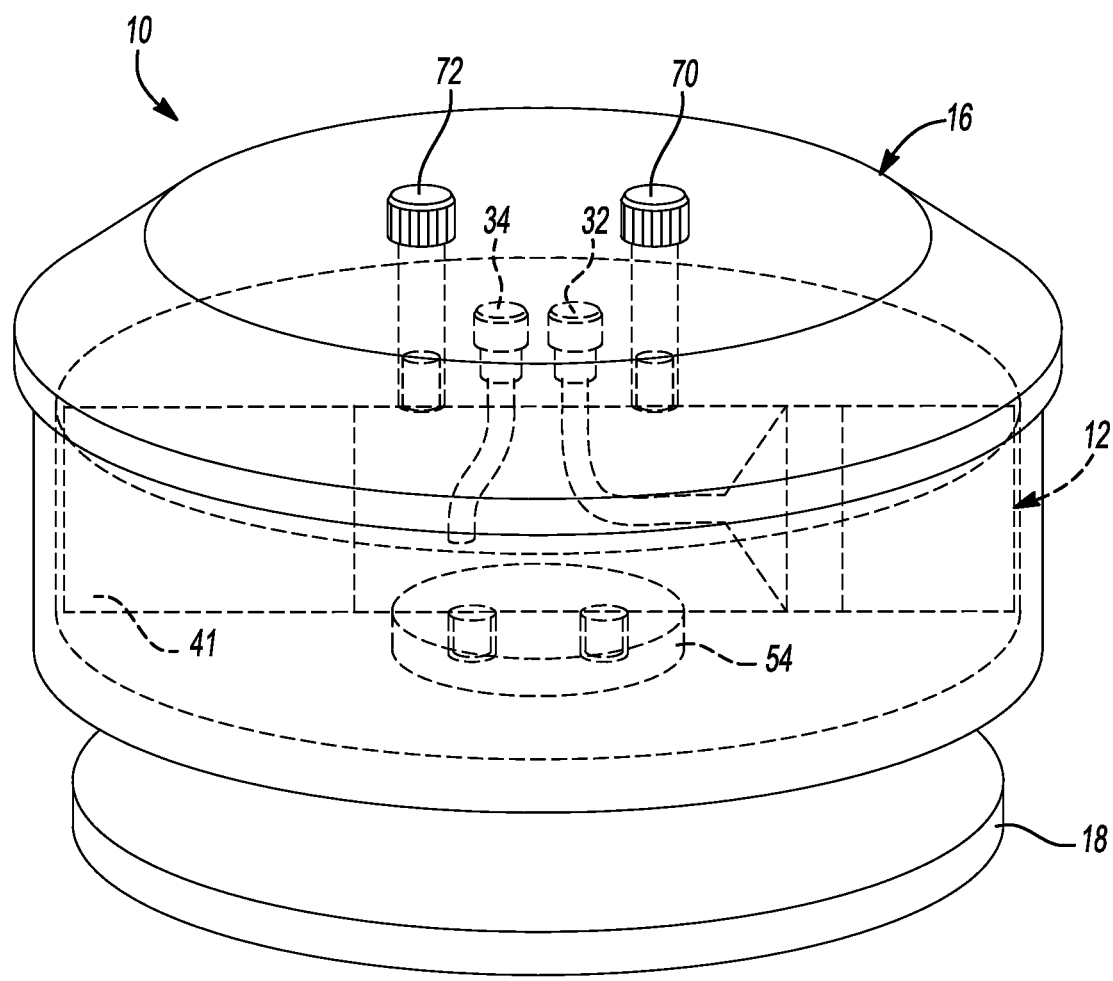
FIG. 1 is a perspective view of a system for separating components of blood according to the present teachings.
Figure 2:
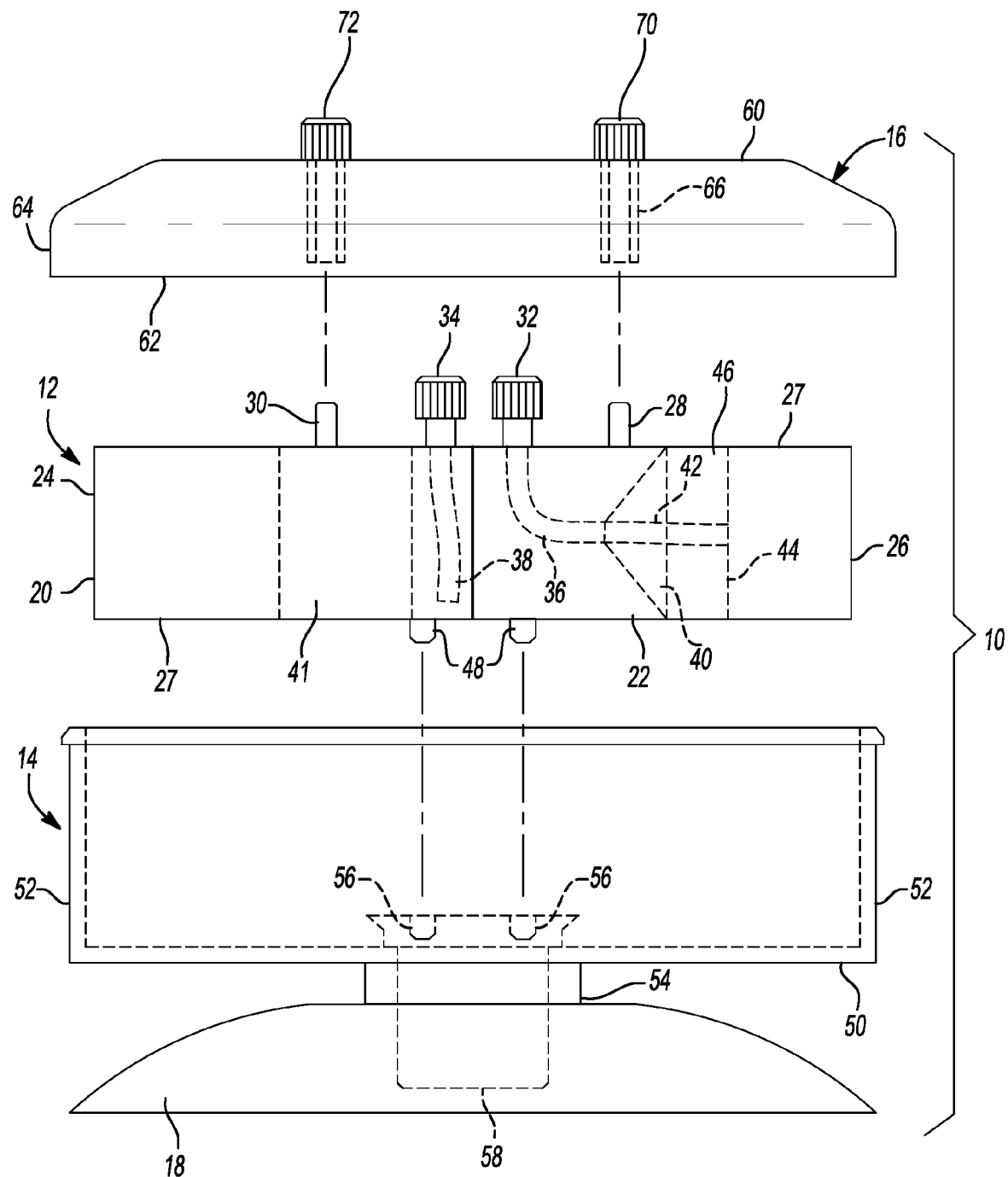
FIG. 2 is an exploded side view of the system of FIG. 1.
Figure 3:
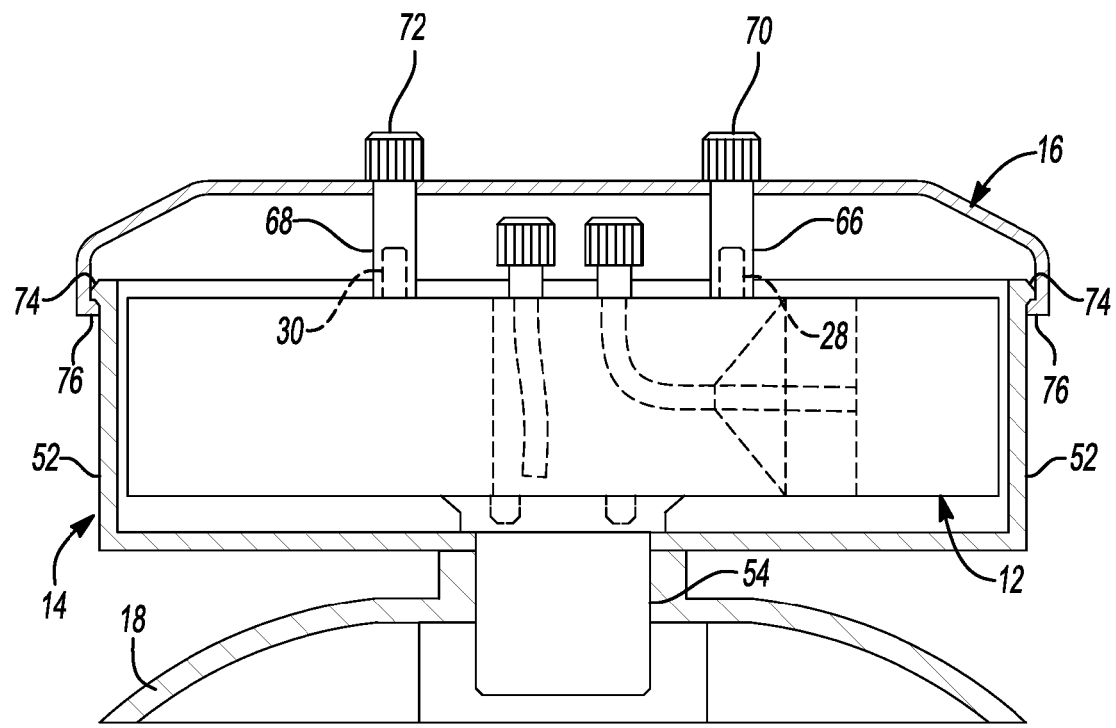
FIG. 3 is an assembled cross-sectional side view of the system of FIG. 1.

A system for separating components of a composition according to density is illustrated in FIGS. 1-3 at reference numeral 10. The system generally includes a component separation device 12, a container 14 for accommodating the separation device 12, a cover 16, and a motorized rotating platform 18. The system 10 can be used to separate components of a variety of compositions, such as whole blood as described herein.

The separation device 12 includes a main body 20 that defines a separation chamber 22. The main body 20 includes a first end 24, a second end 26, and a cylindrical sidewall 27 that extends between the first end 24 and the second end 26. The main body 20 is sized to fit within the container 14. While the separation device 12 described herein is merely an exemplary device, the device 12 is based off the separation devices of Biomet Inc.'s GPS system as described in, for example, U.S. Pat. No. 7,179,391 (filed May 23, 2003) and U.S. Publication Nos. 2005-0109716 (filed Sep. 2, 2004) and 2006-0273049 (filed May 25, 2006), which are hereby incorporated by reference. Differences between the device 12 and the separation tubes of the GPS devices include the location of the outlet ports 32 and 34 at the sidewall 27 and the presence of the locking details 48. In addition to the separation devices of the GPS, any suitable separation device can be used after being modified to include the locking details 48 and the outlet ports 32 and 34.

At the sidewall 27 is a first inlet port 28 and a second inlet port 30. The first and the second inlet ports 28 and 30 extend through the sidewall 27 to permit the introduction of materials into the separation chamber 22. As illustrated, the first and the second inlet ports 28 and 30 extend from the sidewall 27. However, the first and the second inlet ports 28 and 30 can be recesses in the sidewall 27 or can be co-planar with the sidewall 27, for example.

Also at the sidewall 27 is a first outlet port 32 and a second outlet port 34. The first and the second outlet ports 32 and 34 extend through the sidewall 27 to permit withdrawal of materials from within the separation chamber 22. As illustrated, the first and the second outlet ports 32/34 each extend from the sidewall 27 and are each covered with a removable cap. The first outlet port 32 includes a first outlet tube 36 and the second outlet port 34 includes a second outlet tube 38 that extends to within the separation chamber 22. The first outlet tube 36 and the second outlet tube 38 can each be directed to different areas of the separation chamber 22 to facilitate withdrawal of components at different regions of the separation chamber 22.

The separation device 12 can be configured to separate components of various different materials or substances by density. For example, the separation device 12 can be a blood component separation device to separate various components of whole blood by density, such as platelet rich plasma, red blood cells, platelets, and white blood cells. The separation device 12 is illustrated as an exemplary blood component separation device.

For example, as a blood component separation device the device 12 includes a separator (which includes a buoy 40 and a divider 44) and a counter-balance 41 at an end of the separation chamber 22 opposite to the buoy 40. The buoy 40 has a shape that conforms to the interior shape of the separation chamber 22. The buoy 40 has a tuned density that is configured to reach a selected equilibrium position in blood. For example, the buoy 40 can have a density tuned in the range from about 1.06 g/cc to about 1.11 g/cc, which is less than the density of red blood cells of whole blood. The buoy 40 has an access port 42 that extends through the buoy 40. The first outlet tube 36 of the first outlet port 32 is connected to the access port 42 of the buoy 40

Mounted to the buoy 40 is the divider 44. The divider 44 is mounted to an end of the buoy 40 opposite to an end where the first outlet tube 36 enters the buoy 40. The divider 44 is mounted to the buoy 40 to create a collection compartment 46 between the divider 44 and the buoy 40. Components present within the collection compartment 46 can be withdrawn from within the separation chamber 22 through the access port 42, which extends to the collection compartment 46 and is in communication with both the first outlet tube 36 and the first outlet port 32

The buoy 40 is movable within the separation chamber 22 laterally with respect to the first end 24 and the second end 26. When the separation device 12 is at rest, the buoy 40 forms an interference fit with the separation chamber 22 to hold the buoy at a position in the separation chamber 22. When the device 12 is rotated upon the platform 18, buoy 40 moves until it reaches an equilibrium within the composition being separated, such as whole blood. Material present in the separation chamber 22, such as blood, is able to pass between the buoy 40, as well as the divider 44, and the inner walls of the separation chamber 22. Alternatively, the buoy 40 and the divider 44 can have an opening to allow material to move through the buoy 40 and the divider 44.

The sidewall 27 of the main body 20 further includes one or more locking details 48 that are located opposite to the outlet ports 32 and 34. As illustrated, the locking details 48 protrude from sidewall 27. However, the locking details 48 can be of any shape, size, or configuration to provide cooperation with the container 14 and the rotating platform 18 to transfer torque from the platform 18 to the separation device 12.

The container 14 includes a container base 50 and cylindrical container sidewalls 52 that extend around the base 50. The base 50 and the sidewalls 52 define a receptacle sized to receive the separation device 12. The base 50 includes an interface 54. The interface 54 cooperates with the rotating platform 18 and receives the separation device 12 to transfer torque from the rotating platform 18 to the separation device 12. Between the interface 54 and the container 14 is a bushing to allow the interface 54 to rotate independent of the container 14. In particular, the interface 54 includes one or more receptacles 56 at a first end and a bottom portion 58 at a second end that is opposite to the receptacles 56. The receptacles 56 receive the locking details 48 of the separation device 12. The bottom portion 58 cooperates with the platform 18 to transfer torque from the platform 18 to the separation device 12.

The rotating platform 18 can be any suitable torque generating device. For example, the rotating platform 18 can be a Vortech type base by Biomet Biologics, Inc. of Warsaw, Ind.

The cover 16 includes an upper portion 60 and a lower portion 62. Side portions 64 extend between the upper portion 60 and the lower portion 62. A first conduit 66 and a second conduit 68 both extend through the cover 16. The first conduit 66 can include a first cap 70 and the second conduit 68 can include a second cap 72. As illustrated in FIG. 2, when the separation device 12 is seated in the container 14 and the cover 16 is on the container 14, the first conduit 66 is aligned with and connected to the first inlet port 28 and the second conduit 68 is aligned with and connected to the second inlet port 30. The connections between the conduits 66/72 and the ports 28/30 provide passages through the cover 16 to permit the introduction of blood, for example, through the cover 16 and into the separation device 12 when the cover 16 is in place over the device 12. The cover 16 can be independent of the container 14 or mounted to the container 14, such as with a hinge.

As illustrated in FIG. 3, the sidewalls 52 of the container 14 include locking details 74 at the ends of the sidewalls that are opposite to the container base 50. The locking details 74 of the container 14 cooperate with locking details 76 of the cover 16. Thus, the cover 16 is mounted to the container 14. To permit the separation device 12 to freely rotate within the container 14 when the cover 16 is in place, the conduits 66 and 68 are slidably removed to detach the cover 16 from the separation device 12, but not completely removed from the cover 16. In this regard, the passageway through the cover 16 that the conduits 66 and 68 are seated in remains filled so as to restrict the passage of bacteria and non-sterile materials through the cover 16. The cover 16 can also be mounted to the container 14 with a hinge at the sidewalls 52.

Figure 4:
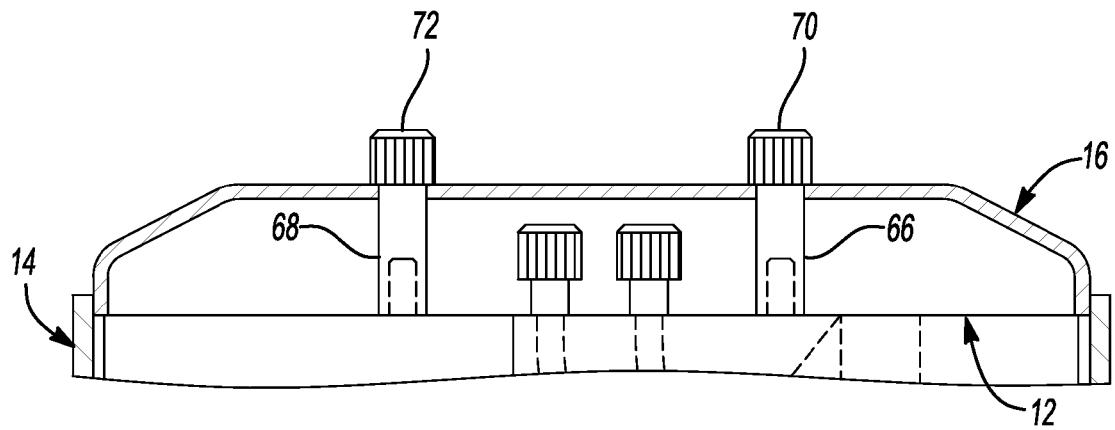
FIG. 4 is a cross-sectional side view of another system for separating blood components according to the present teachings.

With reference to FIG. 4, the system 10 can alternatively be provided with a cover 16 that is directly attached to the separation device 12. As a result, the cover 16 can rotate with the separation device 12 and the first and second conduits 66 and 68 do not need to be detached from the separation device 12 to permit rotation of the separation device 12. A bushing is provided between the cover 16 and the walls 52 of the container to reduce friction and allow the cover 16 to freely rotate within the container 14.

In use, the device 12, the container 14, and the cover 16 are sterilized. The sterile separation device 12 is placed in the sterile container and the sterile cover 16 is seated over the separation device 12 to prevent contamination of the separation device 12. With the separation device 12 sealed within the container 14, the container 14 can be handled by non-sterile personnel. For example, non-sterile personnel can transport the separation device 12 and/or load the separation device 12 with a composition to be separated, such as blood. For example, blood can be inserted into the separation device 12 through the first and/or second ports 28 and 30 using the first and/or second conduits 66 and 68.

After the separation device 12 is filled with blood, the container 14 is seated on the rotating platform 18. The separation device 12 is spun by the platform 18 for a suitable time at a suitable speed to generate a force of about 593×g. After the device 12 is spun as appropriate, the different components of blood will be separated according to density. For example, red blood cells typically settle between the divider 44 and the second end 26, a buffy coat of white blood cells and blood platelets typically settles in the collection compartment 46 between the buoy 40 and the divider 44, and platelet poor plasma typically settles between the counterbalance 41 and the buoy 40.

The sterile container 12 can then be opened and the separation device 12 can be removed by sterile personnel in the sterile environment or simply dumped into the sterile environment, such as onto a sterile tray. The desired blood fraction can be extracted through the first and/or the second outlet ports 32 and 34. For example, if blood platelets are desired to be extracted they can be extracted using the first outlet port 32 because the first outlet port 32, via the first outlet tube 36, extends to the collection compartment 46 where the platelets settle. Using the first outlet port 32, the red blood cells can be subsequently extracted after extraction of the platelets as the red blood cells can be withdrawn through and/or past the divider 44. If the platelet poor plasma is to be extracted, the second outlet port 34 can be used because the second outlet tube 38 extends to the region where the platelet poor plasma typically settles.

Thus, when sealed within the container 14, the sterile separation device 12 can be filled and spun by non-sterile personnel in a non-sterile environment. The container 14 can then be opened and the sterile separation device 12 can be removed and transferred to the sterile environment where the separated components can be withdrawn from the device 12 as necessary. Thus, while in the container 14 the sterility of the device 12 can be maintained even though the device is in a non-sterile environment, which offers greater flexibility for use and transport of the device 12.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A system for separating components of a composition according to density comprising:
    a torque generating device;
    a separation device for separating the composition into different components according to density, the separation device including:
        a first end and a second end opposite to the first end, wherein a longitudinal axis extends between the first end and the second end;
        a sidewall extending between the first end and the second end, the sidewall defining a separation chamber;
        a separator within the separation chamber along the longitudinal axis;
        an inlet port and an outlet port each extending through the sidewall between the first end and the second end; and
        a counterbalance between the second end and the inlet port; and
    a housing that accommodates the separation device to maintain the separation device in a sterile condition when seated therein;
    wherein the torque generating device is external to the housing and is configured to supply torque to the separation device when seated in the housing.

2. The system of claim 1, wherein the torque generating device includes a motorized rotating platform.

3. The system of claim 1, wherein the separator includes a buoy slidable along the longitudinal axis having a density less than that of red blood cells of whole blood.

4. A separation device for separating components of a composition according to density comprising:
    a first end, a second end, a sidewall that extends between the first end and the second end to define a separation chamber, wherein a longitudinal axis extends through the separation chamber between the first end and the second end;
    a separator slidably mounted within the separation chamber along the longitudinal axis and having a density such that the separator is operable to move to an equilibrium between two of the components to be separated after the separation device is rotated;
    a first outlet port including a first outlet tube that extends from a first side of the sidewall and through the buoy to provide fluid communication between an exterior of the separation device and a first area of the separation chamber between the separator and the second end;
    a second outlet port including a second outlet tube that extends from the first side of the sidewall to a second area of the separation chamber that is between the first end and the buoy separator; and
    a coupling device at a second side of the sidewall that is opposite to the first side of the sidewall surface, the coupling device is configured to receive torque generated by a torque generating device;
    wherein upon rotation of the separation device about a midpoint between the first end and the second end along the longitudinal axis in a plane that is perpendicular to a longitudinal axis along which the torque is applied, the separator is operable to separate a first component of the composition having a first density from a second component of the composition having a second density, the first component is isolated in the first area of the separation chamber and the second component is isolated in the second area of the separation chamber.

5. The separation device of claim 4, further comprising an inlet port that provides fluid communication with an interior of the separation device, the inlet port is at the first side of the sidewall and spaced apart from the first and second outlet ports.

6. The separation device of claim 4, wherein a first distance between the first end and the second end is greater than a second distance between the first side of the sidewall and the second side of the sidewall.

7. The separation device of claim 4, wherein the separator further includes a buoy and a divider that is spaced apart from the buoy and mounted to the buoy to define a collection compartment between the divider and the buoy; wherein the first outlet tube extends across the collection compartment to the divider.

8. A device for separating components of a composition according to density comprising:
    a separation device including:
        a first end, a second end opposite to the first end, a cylindrical sidewall extending between the first end and the second end to define a separation chamber, and a longitudinal axis extending through an axial center of the separation chamber from the first end to the second end;
        a counter-balance within the separation chamber and proximate to the first end;

a separator including a buoy within the separation chamber and slidably mounted along the longitudinal axis between the second end and the counter-balance;

a divider mounted to the buoy at a side of the buoy proximate to the second end, the buoy has a density such that it is operable to move to an equilibrium between two of the components to be separated;

a first outlet port including a first outlet tube that extends from a first side of the sidewall to the divider, the first outlet tube extends through the buoy;

a second outlet port including a second outlet tube that extends from the first side of the sidewall to a location within the separation chamber that is between the counter-balance and the buoy;

an inlet port that provides fluid communication between an exterior of the separation device and the separation chamber, the inlet port is at the first side of the sidewall and spaced apart from the first and second outlet ports; and a locking device at a second side of the sidewall that is opposite to the first side and is operable to cooperate with a rotating platform to rotate the separation device; and an outer housing including a base and a sidewall that define a receptacle that accommodates the separation device and includes an interface operable to transfer torque from the rotating platform to the separation device when the separation device is seated in the receptacle;

a cover configured to engage the outer housing to provide a seal therebetween and maintain the separation device in a sterile condition when seated within the receptacle, the cover includes a conduit extending therethrough, the conduit is operable to cooperate with the inlet port when the separation device is seated in the receptacle to permit introduction of the composition through the cover and into the separation device through the inlet port while the separation device is maintained in a sterile condition;

wherein the rotating platform is external to the outer housing and is selectively coupled to the outer housing at the interface to supply torque to the separation device; and wherein upon rotation of the separation device by the rotating platform about a midpoint between the first end and the second end along the longitudinal axis in a plane that is perpendicular to a longitudinal axis along which the torque is applied and restricting rotation of the separation device about the longitudinal axis, the separator is operable to separate a first component of the composition having a first density from a second component of the composition having a second density, the first component is separated in a first area of the separation chamber between the divider and the first end and the second component is separated in a second area of the separation chamber between the divider and the second end.

9. The system of claim 1, wherein the sidewall is cylindrical and the longitudinal axis extends through an axial center of the separation chamber.

10. The system of claim 1, wherein the sidewall includes a locking device that is at a first portion of the sidewall opposite to a second portion of the sidewall including the inlet port and the outlet port, the locking device is configured to engage an interface at a base of the housing that transfers torque from the torque generating device to the housing.

11. The system of claim 1, wherein the housing further comprises:
a base;

a cover configured to selectively engage one of the separation device or the housing to provide a seal therebetween that maintains the separation device in a sterile condition when seated in the housing; and a conduit extending through the cover and in communication with the inlet port for introducing the composition into the separation device without opening the cover to maintain the separation device in a sterile condition as the composition is introduced;

wherein the torque generating device is external to the housing and selectively coupled to the housing at the base.

12. The system of claim 11, wherein the cover is mounted directly to the separation device and rotates with the separation device.

13. The system of claim 11, wherein the cover is mounted directly to the housing and is stationary when the separation device is rotating.

14. The system of claim 11, wherein the conduit is movable to selectively engage and disengage the separation device without removing the cover.

15. A system for separating components of a composition according to density comprising:

A separation device including:
A first end and a second end opposite to the first end, wherein a first longitudinal axis extends between the first end and the second end;
A sidewall extending between the first end and the second end, the sidewall defining a separation chamber;
A movable buoy within the separation chamber for separating components of the composition according to density; and
An inlet port and an outlet port each extending through the sidewall between the first end and the second end;

A housing including a base, a housing sidewall extending from the base, and a cover, the housing defines a compartment configured to receive the separation device therein such that the first longitudinal axis is substantially parallel to the base, and maintain the separation device in a sterile condition; and A torque generating device external to the housing and selectively coupled to the housing to transfer torque to the separation device when seated in the compartment to rotate the separation device about a midpoint between the first end and the second end along the first longitudinal axis in a plane that is both substantially perpendicular to a second longitudinal axis along which the torque is applied and substantially parallel to the base.

16. The system of claim 15, wherein a first distance between the first end and the second end is greater than a second distance between opposing sides of the sidewall.

17. The system of claim 15, wherein the sidewall is a cylindrical sidewall.

18. The system of claim 15, wherein the movable buoy includes a buoy movable along the first longitudinal axis.

19. The system of claim 15, further comprising a counter-balance within the separation chamber at the second end, the separator is closer to the first end than to the second end.

20. The system of claim 15, further comprising a conduit extending through the cover and in communication with the inlet port for introducing the composition into the separation device without opening the cover to maintain the separation device in a sterile condition as the composition is introduced, the conduit is movable to selectively engage and disengage the separation device without removing the cover.

* * * * *

UNITED STATES PATENT AND TRADEMARK OFFICE
CERTIFICATE OF CORRECTION

PATENT NO. : 8,518,272 B2  Page 1 of 1
APPLICATION NO. : 12/062801
DATED : August 27, 2013
INVENTOR(S) : Jacy C. Hoeppner It is certified that error appears in the above-identified patent and that said Letters Patent is hereby corrected as shown below:

In the Claims

Column 6, Claim 4, Line 27, after "the", delete "buoy"

Column 6, Claim 4, Line 29, after "sidewall", delete "surface"

Signed and Sealed this
Eighteenth Day of November, 2014

Michelle K. Lee
*Deputy Director of the United States Patent and Trademark Office*